US00PP21304P3

(12) United States Plant Patent
Rogmans

(10) Patent No.: US PP21,304 P3
(45) Date of Patent: Sep. 21, 2010

(54) *FALLOPIA* PLANT NAMED 'IGNISCUM'

(50) Latin Name: *Fallopia sachalinese*
Varietal Denomination: Igniscum

(75) Inventor: Maria Rogmans, Kalkar (DE)

(73) Assignee: Conpower Energie GmbH & Co KG., Munich (DE)

( * ) Notice: Subject to any disclaimer, the term of this patent is extended or adjusted under 35 U.S.C. 154(b) by 0 days.

(21) Appl. No.: 12/069,926

(22) Filed: Feb. 14, 2008

(65) Prior Publication Data

US 2008/0201811 P1 Aug. 21, 2008

(30) Foreign Application Priority Data

Feb. 15, 2007 (QZ) ..... 2007/0149

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Susan B McCormick Ewoldt
(74) *Attorney, Agent, or Firm*—Laurence A Greenberg; Werner H Stemer; Ralph E Locher

(57) ABSTRACT

A new and distinct cultivar of *Fallopia sachalinese* plant named 'Igniscum'; characterized by foliage which is elliptical, with an acuminate shape at the top, a straight line at the lower region, a leaf color of green-group 135C with a velvety upper surface texture at leaf maturity. The lower surface is coriaceous, the leaves are very firm and with a film providing a slightly wet appearance. The margins of the leaves are smooth, the lateral nerves connect at the side of the leaf in an inverted V-shaped structure. The leaf stalks are red-purple-group 59B even at maturity. The blossoms are orange-white-group 159C.

9 Drawing Sheets

Latin name of the genus and species of the plant claimed: Botanical classification: *Fallopia sachalinese.*

Cultivar designation: 'Igniscum'.

BACKGROUND OF THE INVENTION

Field of the Invention

The present invention, 'Igniscum' relates to a new and distinct cultivar of Japanese Knotweed *Fallopia* or Mexican Bamboo/Round Knotweed, botanically known as *Fallopia sachalinese* and hereinafter referred to as 'Igniscum.'

The *Fallopia sachalinese* plant is native to Sakhalin Island in the South Kuril Islands and over the years became naturalized in Europe. The species *Fallopia sachalinese* is a variety that was discovered in the wild, is particularly fast-growing, has no tillers, is hardy and is a producer of a great deal of biomass. The new variety of *Fallopia sachalinese* was discovered in 1987 at the location of the breeder, in North-Rhine-Westfalia, Germany, as a spontaneous branch mutation of the original *Fallopia sachalinense* with differences in the exterior and in the roots and the seeds. Isolation/separation from other plants and development of the species was then carried out at the breeder's location over 20 years, during which the entire procedure was kept secret. Only the method of division of parts of the roots was used for regeneration, because the new species is not intended to produce seeds. In other words, only the best of the best of the vegetatively produced new young plants obtained from a mother plant were selected for new generation for further reproduction. In this way, the new features of the new variety became more and more established. Asexual reproduction was observed at the breeder's location since the mother plant of this variety was discovered in 1987. Asexual reproduction was then stabilized or established by only vegetative production of the new generation. The original plant was discovered in 1987, but was not in a state that was ready for a new variety, because newly occurring observable features had to be developed and stabilized, in order to prevent a return to well-known negative features of invasiveness. This stabilization had to be done by conventional non-genetic, non-crossbreeding development. The development steps were carried out by selection of the best of the best in each generation, and stabilization of temporarily degenerative behavior in growth of fortunately only one generation in 1999. The character of the area in which the 'mutated' plant was discovered was open land, near a forest in the Xanten region, which is close to in Kalkar stated below, the final breeding home of the finally developed new variety 'Igniscum'. The area was a landscape in which further knotweed is found, but no other plants were found near (within one hundred meters) the original plant that was discovered. The first asexual reproduction with vegetative cuttings of the new variety 'Igniscum' took place at Kalkar, Germany. Furthermore, a development timeline may be divided into segments. So far, only a few plants have been vegetatively generated from one generation. The breeder used the technique of producing young plants obtained root parts from the mother plant. These young plants and their following generations were no longer produced from root cuts beginning from the year 2002. They have been produced from that time as so-called shoots, which are obtained from vegetative cuttings. These vegetative cuttings are then cultivated until they produce small roots themselves and then they are planted into plantation.

The following is the history of the breeding, origin, mutation and generative selective breeding of the plant:

The original plant out of which the new variety 'Igniscum' was bred (only by selective breeding that is generation by cutting new young plants grown out of root cuts from a mother plant) was discovered in the wild in 1987. This basic plant was discovered as a natural mutation of *Fallopia sachalinense*. In other words, the plant was completely atypically alone standing. Known knotweed plants in the wild never stand alone. This fact, and the fact that there were no running roots near the plant, provided a first hint about sterility (no active seeds) and non-invasivity. The plant was therefore removed from its location by excavation. It was also known, that *Fallopia sachalinense* is spread over Europe. The breeder therefore found several differences in the exterior of the plant, meaning that it only could be a hybrid. Then the breeder separated the basic plant and found that it is sterile, and bred it by only vegetative regeneration. No crossbreeding and no genetic manipulation was made. The breeder had to assume, that it was already a hybrid, which was crossbred in nature, a long time ago.

By only selective breeding, which means selection of the best of the best of the vegetatively regenerated young plants, obtained from the mother plant, some typical features were developed and stabilized to reach the species we have today named 'Igniscum'.

Therefore, as a result, the new variety 'Igniscum' is based on the original *Fallopia*, but had already mutated or crossbred in nature, and several definitive features developed due to the very long time taken for selective breeding by selection and cutting and selection and cutting, etc.

Accordingly, the new variety 'Igniscum' is a result of branch mutation, but crossbreeding was made by nature before it was discovered, since the basic mother plant which was discovered was already a mutated *Fallopia sachalinense.*

It was also verified by 25 tests, that the new variety 'Igniscum' remains sterile (with practically no regeneration from seeds) has no running roots and is therefore not invasive. Additionally, the exterior features are very different from the original plant *Fallopia sachalinense*, and are a further result of the long-time regenerative selective breeding of the new variety 'Igniscum'.

The tested the new variety 'Igniscum' plants were extremely homogeneous. The features describe a plant of one year of age (1.5 meters high). Therefore, after one year it was not fully mature, but already had all of its visible typical features.

As a result, the new variety 'Igniscum' today represents a calm, non-invasive new species of *Fallopia* which, in contrast to the wild species, can be planted in large fields.

The nomination of the new species, tested at the CPVO (EU Community Plant Variety Office) is 'Igniscum' or *Fallopia* 'Igniscum'. This was the nomination in Europe given by the CPVO.

The result of this development was that this new species, designated 'Igniscum' by the inventor, had lost its detrimental characteristic of being invasive. In other words, the new variety 'Igniscum' is not invasive due to the fact that it has no running or invasive roots, and no seeds or only very few seeds. This means that the new variety 'Igniscum' can now be cultured normally on a large plantation because it is non-invasive. This is a very important, new and surprising feature which makes the new variety 'Igniscum' very different from its genetic *Fallopia sachalinense.*

The new variety 'Igniscum' is maintained by using asexual propagation methods, e.g. cuttings, meristem propagation and cell cultures in Germany, as mentioned above.

Due to this special unusual feature of the new variety 'Igniscum', of it only being possible to be reproduced through asexual propagation, which is completely different from the original *Taxon* species, genus *Fallopia sachalinense*, the new variety 'Igniscum' is non-invasive.

Therefore, it is a surprising result that the requirement for asexual propagation leads to the extremely advantageous effect of non-invasiveness. This is surprising because the genus species *Fallopia sachalinense* plant is believed to be the most invasive plant on earth, while the new variety 'Igniscum' is not invasive. Due to this fact, the new variety 'Igniscum' can be cultured on large, open terrain.

Furthermore, the new 'Igniscum' plant variety is extremely uniform and stable, which has been verified during the last 20 years of development of the plant.

With regard to reproduction, experience has shown the plant to be sterile. Genuine propagation can only be accomplished by shoots, meristem propagation or cell cultures.

Exploitation of the plant is as an industrial crop or energy crop, which is usable in biological plant protection and in health care.

Regarding duration of the culture, the plant is a perennial species. The inventor has been experimenting with the plant for 20 years and has seen that the biomass yield increases annually. *Fallopia sachalinense* has been known to be a wild species to this day.

The inventor is not aware of any addresses and collections of varieties.

BRIEF SUMMARY OF THE INVENTION

The plants of the new variety 'Igniscum' have been observed repeatedly for twenty years as having unique traits. These characteristics, in combination, distinguish the new variety 'Igniscum' as a new and distinct cultivar, as follows:

1. The foliage of the new variety 'Igniscum' is elliptical, with an acuminate shape at the top, a straight line at the lower region, a leaf color of 135C with a velvety upper surface texture at leaf maturity. The lower surface is coriaceous, the leaves are very firm and with a film providing a slightly wet appearance. The margins of the leaves are smooth, the lateral nerves connect at the side of the leaf in an inverted V-shaped structure. The leaf stalks are red-purple-group 59B even at maturity. The leaf size varies between a breadth of 13 cm and a length of 21 cm and a breadth of 17 cm and a length of 22 cm. The blossoms are orange-white-group 159C. Leaf size: Leaf size varies between a breadth of 13 cm and a length of 21 cm and a breadth of 17 cm and a length of 22 cm. Leaf form: Elliptical, with an acuminate shape at the top, straight line at the lower region and a velvety upper surface texture at leaf maturity. Lower surface coriaceous, the leaves are very firm and with a film providing a slightly wet appearance. The margins of the leaves are smooth, the lateral nerves connect at the side of the leaf in an inverted V-shaped structure. Leaves: simple alternate; petiole, short, up to 3 cm long, green-group N134A with medium red-purple-group 59B anthocyanin coloration, color changes along the length from red-purple-group 59B to yellow-green group 146B; blade up to approximately 16-21 cm long and up to approximately 11-14 cm broad, ovate, grey-brown-group 199A, approximately 137 A, but greener, weakly concave, margin entire, main vein yellow-green group 146B, top acuminate, base truncate, lower side yellow-green group 145B to 145C. Leaf color: The fresh new shoots in spring are red-purple-group 59B. The vein color is green-group 130D to gray-green group 191A. The upper surfaces of the leaves are between green-group 135C and green-group N134A. The caulis is green-group N134A. The caulis with a coverage of grease-like rime protecting the plant is gray-green-group 191A.

2. The height of the new variety 'Igniscum' plant is 3-4 m.
3. The new variety 'Igniscum' plant has a hollow stem with internodal segments, high fiber content and lignification in late summer/autumn.
4. The new variety 'Igniscum' plant has no tillers and its rootstock reaches down to a depth of 2 m. There are 30-100 stems per plant and approximately 20-22 nodes.
5. The blooming time, depending on the weather, may start in July, but is usually between August and November.

BRIEF DESCRIPTION OF DRAWINGS

The colored photographs described below illustrate the overall appearance of the new cultivar, showing the colors as true as it is reasonably possible to obtain in such colored reproductions. The colors in the photographs may differ from the color values mentioned in the detailed botanical description, which accurately describes the colors of the new variety 'Igniscum' plant. The age of the plants in the photographs is 2-3 years.

BOTANICAL DESCRIPTION OF THE PLANT

Figure 1:
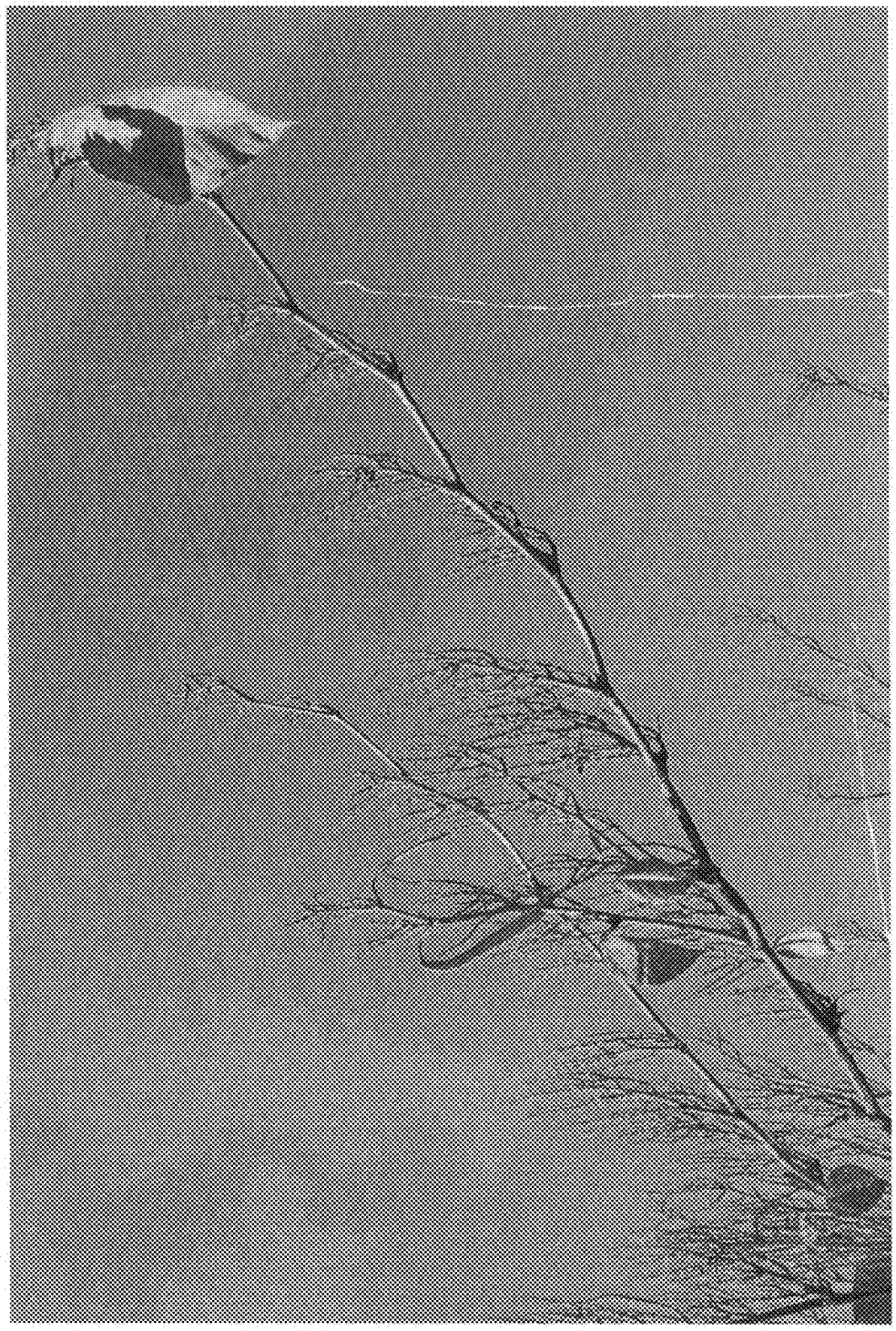
FIG. 1 is a photograph showing a branch of the new variety 'Igniscum'.
Figure 2:
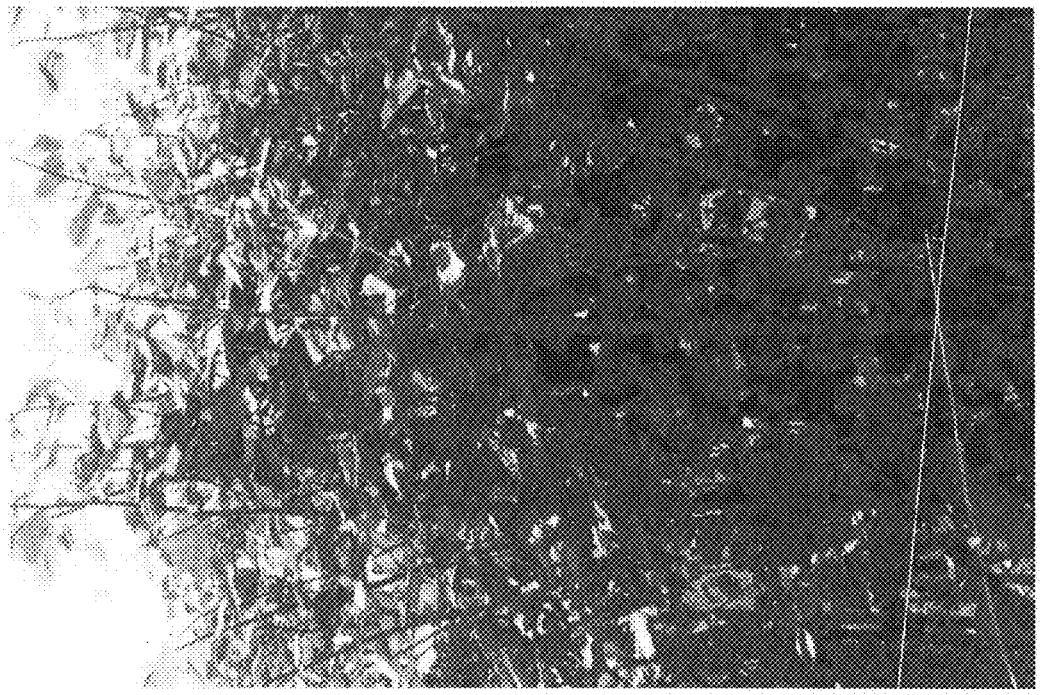
FIG. 2 is a photograph showing several of the new variety 'Igniscum' plants.
Figure 3:
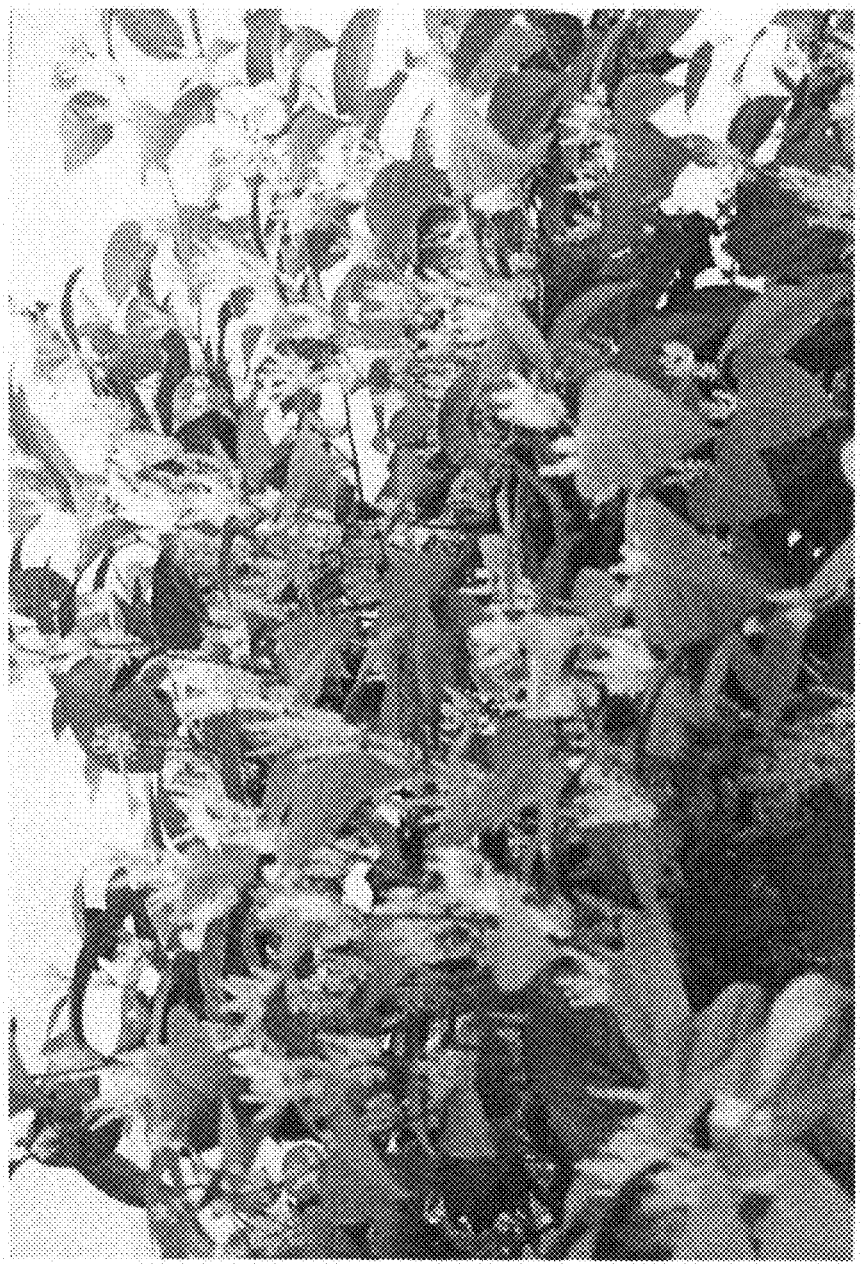
FIG. 3 is a photograph showing an enlarged view of the flowers of the new variety 'Igniscum'.
Figure 4:
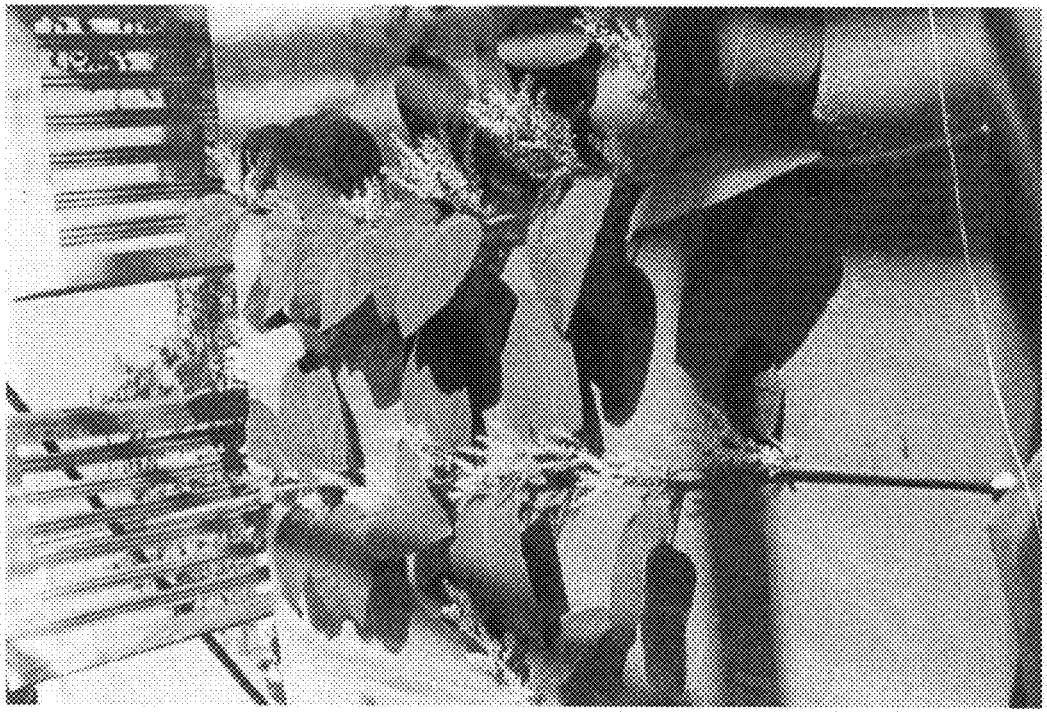
FIG. 4 is a photograph showing an enlarged view of a branch of the new variety 'Igniscum'.
Figure 5:
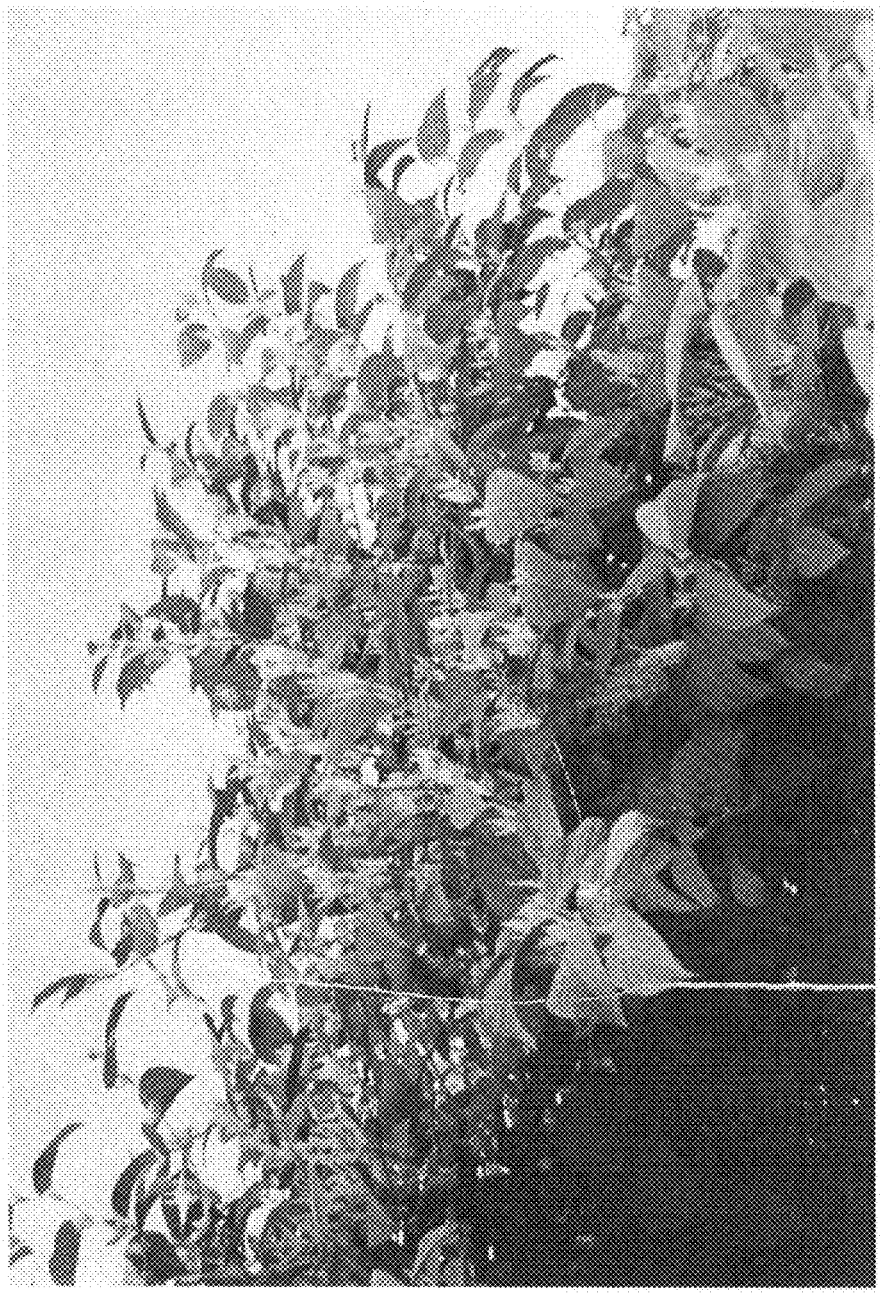
FIG. 5 is a photograph showing a view of the new variety 'Igniscum' similar to FIG. 3 on a reduced scale.
Figure 6:
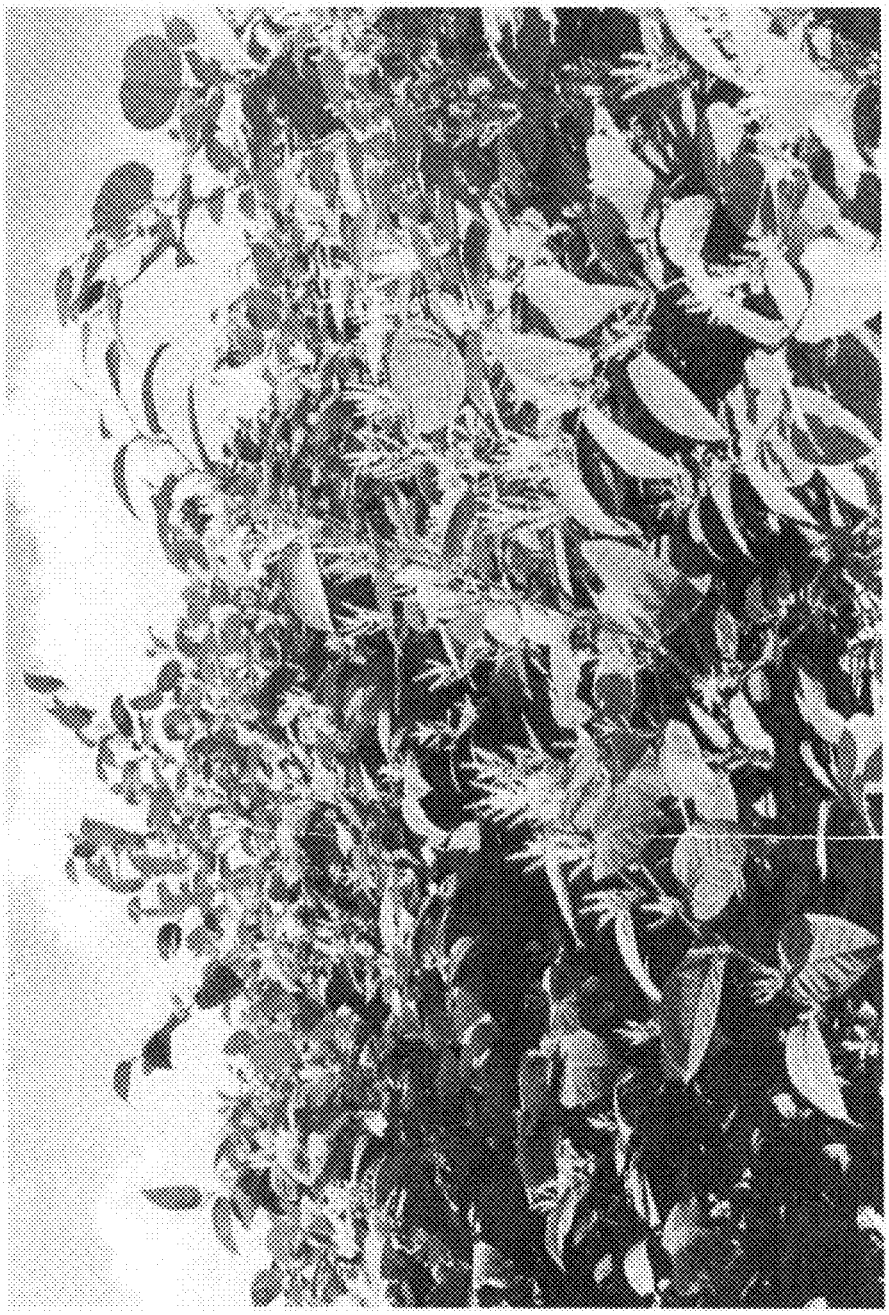
FIG. 6 is a photograph showing another view of the new variety 'Igniscum' similar to FIG. 3.
Figure 7:
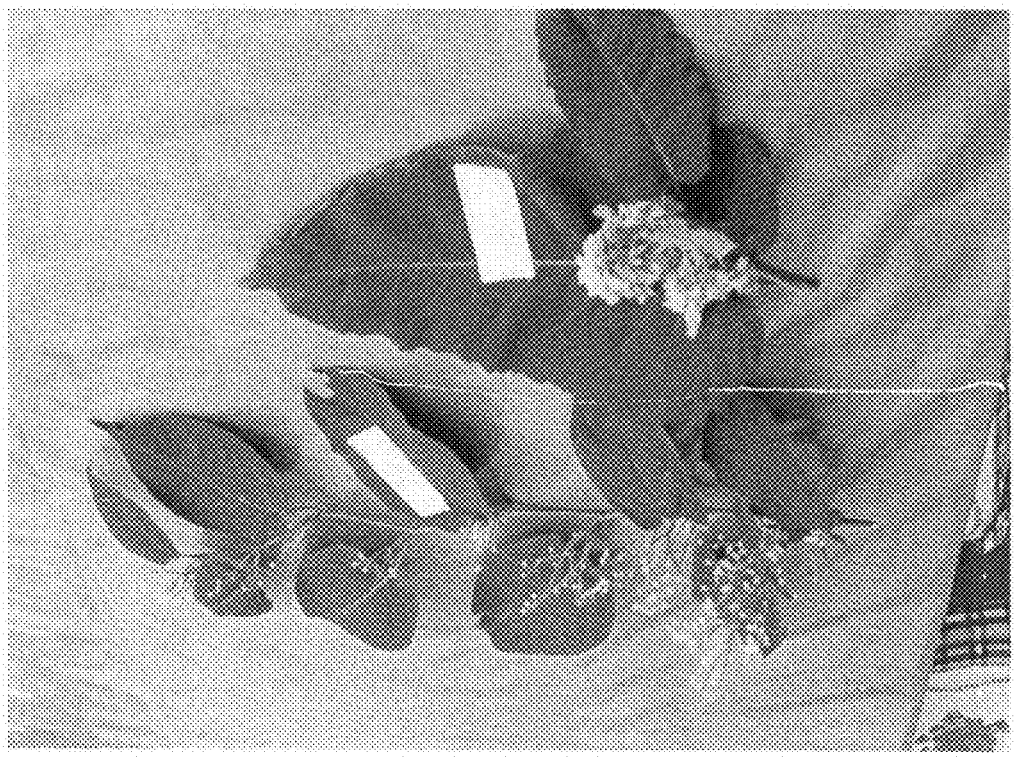
FIG. 7 is a photograph showing an enlarged view of several leaves of the new variety 'Igniscum'.
Figures 8A, 8B, 8C:
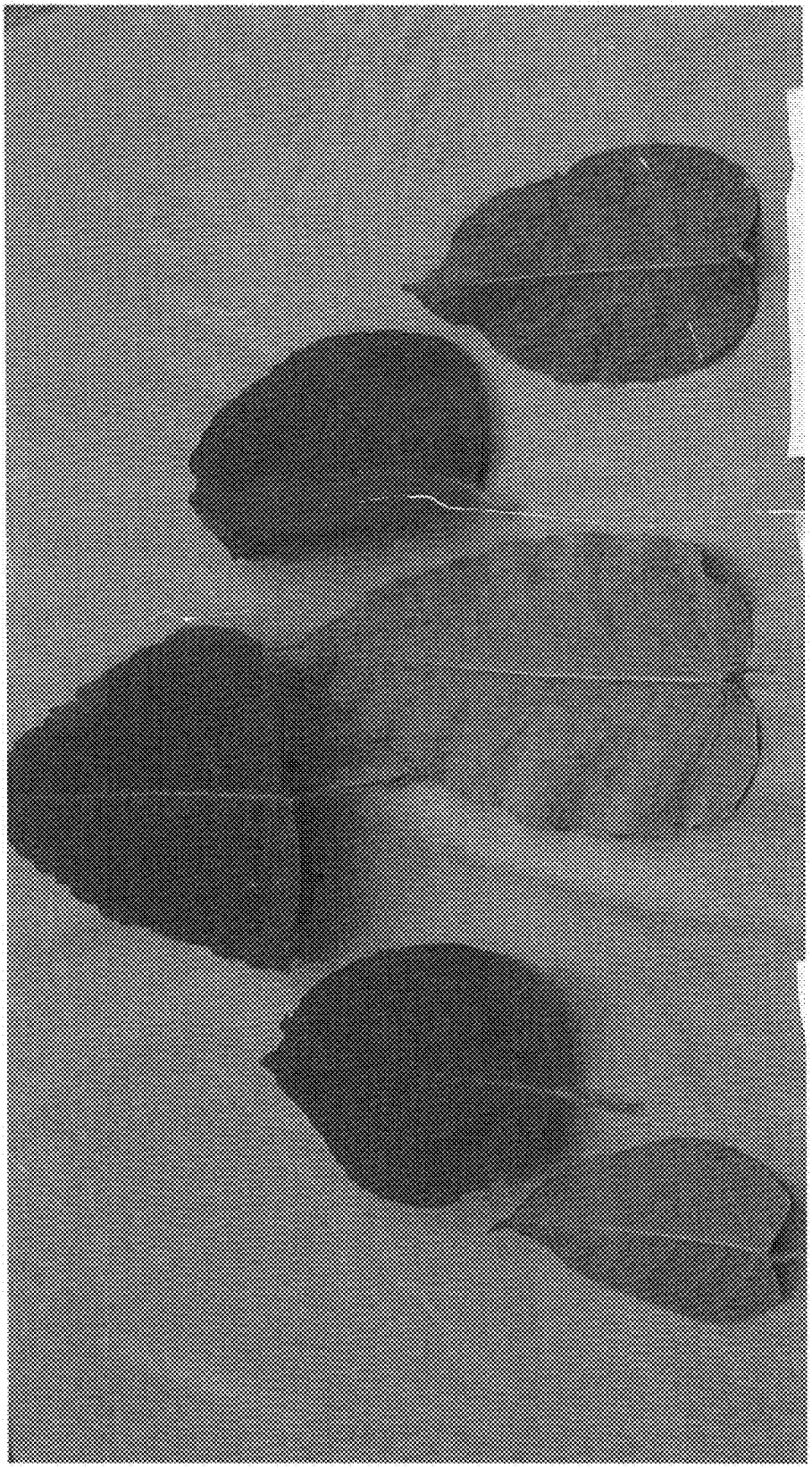
FIG. 8A (to the left) shows the upper and lower leaves of *Fallopia sachalinense*, FIG. 8B (middle) shows the upper and lower leaves of the new variety 'Igniscum', and FIG. 8C (to the right) shows the upper and lower leaves of another *Fallopia* variety 'Candy'.
Figure 9:
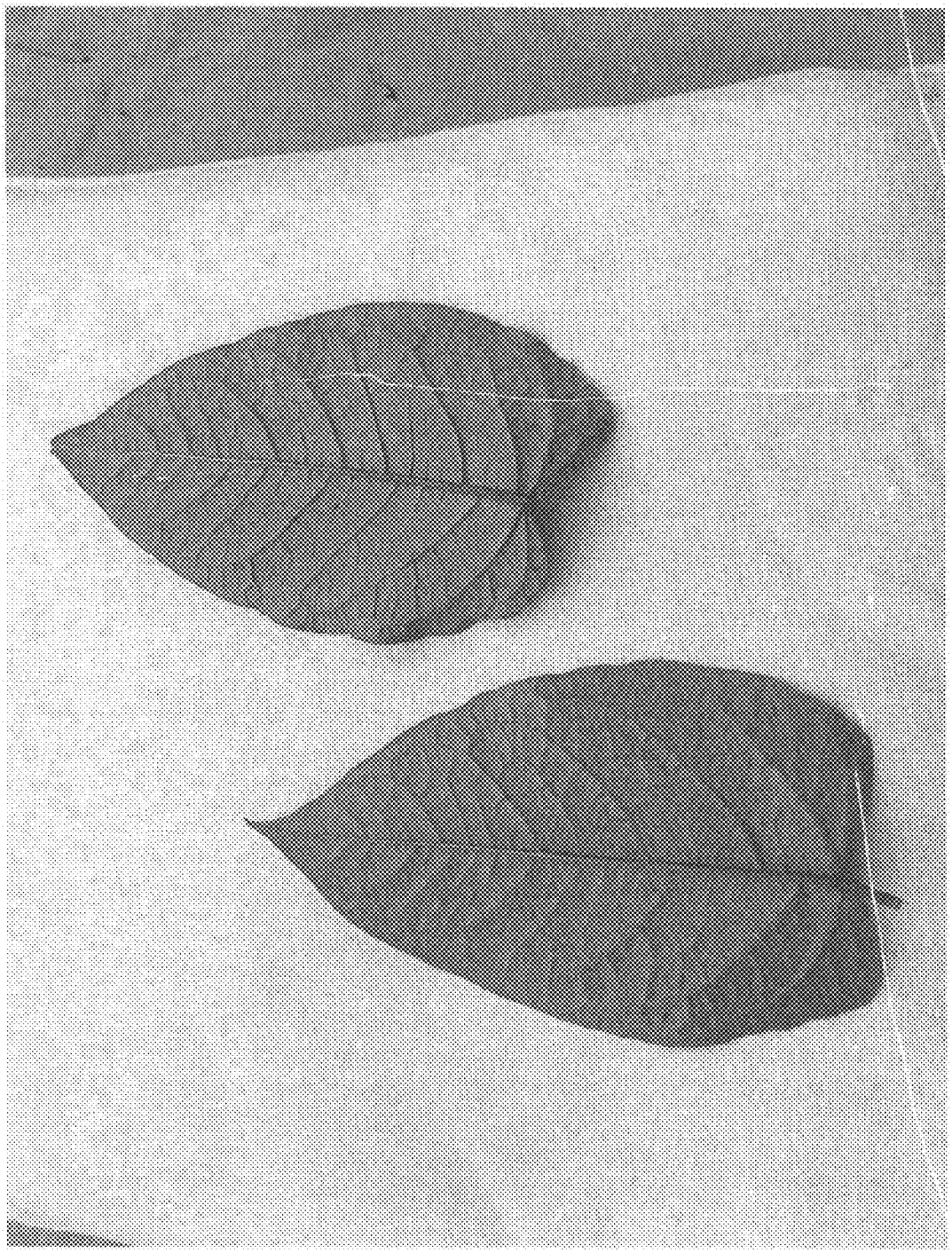
FIG. 9 is a photograph showing an enlarged view of the lower surface of the leaves of the new variety 'Igniscum'.

The following detailed description of the new cultivar 'Igniscum' is based on observations of the plant and color references are made to The Royal Horticultural Society Colour Chart, except where general terms of ordinary dictionary significance are used.

Height of the plant: 3-4 m; Width of the plant: 1-3 m.

Site: Bright, sunny site, light to heavy soils.

Habit: No tillers, rootstock reaches down to a depth of 2 m.

Number of stems: 30-100 stems per plant.

Constitution of stem: Hollow with internodal segments, high fiber content, lignification in late summer/autumn.

Color of stem: green-group N134A with a slight gray shade and red-purple-group 59B colored dots that stretch to form lines, ceraceous layer.

Circumference of stem:

*At the base.*—12.50 cm.
*At a height of* 1 *m.*—11.00 cm.
*At a height of* 2 *m.*—630 cm.
*At a height of* 3 *m.*—314 cm.
*At the top.*—100 cm.

Diameter of the stem:

*At the base.*—3.8-4.00 cm.
*At a height of* 1 *m.*—3.5 cm.
*At a height of* 2 *m.*—2.0 cm.
*At a height of* 3 *m.*—10 cm.
*At the top.*—0.3 cm.

Distance between nodes: Beginning with the stem, the distance between nodes starts with a distance of 16.5 cm and, with further narrowing of the stem, ends at 3 cm at the top. The stem has a membrane inside at each node dividing the stem into chambers.

Number of nodes There are approximately 20-22 nodes.

Lateral shoots: The lateral shoots are produced on the upper third of the stem. They have a length of approximately 0.45 cm-1.50 m. There are approximately 18-23 lateral shoots on each stem.

Plant: 1.2 m high and 1.5 m broad (young plant), lower part stem branched; at base up to 6-7 mm thick and lignified, yellow-green group 146B, with weak red-purple-group 59B spots; internodes approximately 8-12 cm long; nodes at the top with weak to medium red-purple-group 59B anthocyanin coloration, at base with grey-brown-group 199C to green-brown-group 200C coloration.

Inflorescence: Upstanding (erect) panicle; peduncle branched, up to approximately 8-11 cm long, yellow-green group 146B; bracts small, green-brown-group 200C; pedicel approximately 6 mm long, yellow-green group 146B; perianth 5-parted, in cross-section 4-5 mm, green-group 130D, approximately RHS 155 A, with green-group N134A flush; stamens 8 in number; filaments approximately 3 mm long, green-group 130D; style small, grey-brown-group 199C. The plants flowers are dioecious with those described herein being female. It is noted that the colors can also differ due to a different constitution of the field. Therefore, all of these colors are only approximate and can change accordingly to the minerals in the ground. These colors are only for further orientation of the exterior of the young plant.

Bloom:

*Form.*—Candle flame-shape.
*Size.*—10 to 20 centimeters.
*Number of blossoms.*—Between several hundred and one thousand.
*Bloom time.*—Middle of August to middle of September.

Blossom and petal description: The florescence of the Plant is an upstanding (erect) panicle, with a hundred or more small blossoms. Each blossom is 2-3 millimeters, and round or slightly oval. Each blossom has two petals. Each of these two petals forms a very small round bag. Several petals (at least 2) are in each blossom and surround the female pistil. If there are only 2 petals in each blossom, they form the shape of an open bag around the pistil. If there are more than 2 petals, they are arranged around the pistil. At the end of the flowering period, the pistil is rebuilt to a little brown nut which is a sterile fruit, because the plant is only female. The petals then surround the nut in the shape of a bag which is partly closed. Each petal, that is each side of the bag, is orange-white-group 159C, sometimes having a type of very small nut therein. The fertility of the nuts is zero. They are more than 96% sterile. The remainder has a fertility of 4% only under the best laboratory conditions. During 20 years, there has been no fertile activity of the seeds observed on the field under natural conditions. The plant produces no fruit. The plant is winter hardy and heat tolerant.

Fresh biomass: Approximately 100 stems were harvested in an experimental harvest in the presence of an independent reviewer. The yield of fresh biomass amounted to approximately 80 kg per plant. The date of the experimental harvest was Aug. 10, 2006.

Dry biomass: Dry biomass (including leaves) is estimated to amount to approximately 20% of the calculated fresh biomass (harvest in late summer/beginning of autumn=mid-September-end of October). No leaves are left when harvesting in January. This means that the crop yield is reduced to the already dried stems.

Cold hardiness: *Fallopia* biomass which has grown early in spring is generally prone to late frost damage. However, later plant growth makes up for the loss. It has been noticed on the experimental field over a longer period of time that the new variety 'Igniscum' survived these annually recurring late frosts without noticeable frost damage.

Seed: The plant produces a very small amount of seed. Long-term observation showed that the seed does not germinate. It is, apparently, sterile. The seed has an imperfectly round or imperfectly elliptical small nut-like shape. Number: one seed nut is located in each blossom. Size: approximately 1 millimeter. Color: between dark brown 165A and brown N199C.

Blooming time: Depending on the weather, blooming may already start in July. Usually, blooming time is between August and November. The new variety 'Igniscum' is an excellent bee plant because of its late blooming time.

The following information is taken from the Plant Primer Instructions for Planting and Cultivation of the new variety 'Igniscum':

The new variety 'Igniscum' is an energy crop belonging to the field of renewable primary products with unique properties, which should be exploited for the purpose of sustainable energy supply.

Preparation of the Field a) Site requirements

The new variety 'Igniscum' requires a soil quality of at least 30-50 soil points, however, not only on the surface but also at a depth of 0.70 m. The soil conditions should be moist, deep, and without water-logging.

It is strongly recommended not to use soils in the proximity of rivers or waters (due to the danger of flooding, wash-out and soil erosion). It is important that no parts of the plant or its roots be in contact with watercourses.

It is advantageous for the cultivation of the new variety 'Igniscum' to use mild clay soils with humid up to very humid conditions, because sufficient supply of water is vital for successful cultivation and high crop yield. Annual precipitation of at least 440 mm is a precondition in this context. The fast-growing new variety 'Igniscum' prefers nutritious, well-aired soils that warm up quickly in spring.

Fields planted with the new variety 'Igniscum' should be cultivated in sites having a soil depth of at least 70 cm, a soil value number of at least 30 soil points, and the soil should have a pH value of between 5.5 and 6.5. It is not recommended to cultivate fast-growing 'Igniscum' if the soil value number is below 30 soil points, unless one accepts a lower production of biomass.

For wind-exposed sites, it is recommended to grow a shelterbelt with, for example, *Miscanthus sin. Giganteus* or other species.

b) Soil preparation

The area to be cultivated should have been treated with alfalfa or identical nitrogen collecting plants in the previous year. Before planting, it is recommended to provide a winter furrow, and, before planting, to harrow the dry soil (harrow or power harrow) in spring. Before planting, the soil should be aerated up to a depth of 10-25 cm.

Directly before planting, green manure is sprayed with herbicides such as 'Basta'.

A soil sample to test for N is taken directly before planting in order to allow additional manuring before the start of the growing season.

The soil must be analyzed annually for N, P, K (N on an annual basis, P and K every 2-3 years) before the start of the growing season.

Possible forms of N doses:
Deposit of N fertilizer
2-3 doses of liquid manure
Dung
Mineral fertilizer (e.g., KAS)

Doses of manure (dry matter harvest in the spring without leaves)
N. 30-50 kg/ha
1. $P_2O_5$ 30-50 kg/ha
2. $K_2O$ 50-100 kg/ha
Liquid manure
Dung
Mineral fertilizer
Doses of manure:
Reserve fertilizing
In the year of planting: 16 g N/m2=160 kg N/ha
under extensive production conditions: 24 g N/m2=240 kg N/ha
under intensive production conditions: 30 g N/m2=300 kg N/ha The required doses of manure can be applied very well by using compost/sewage sludge (of guaranteed quality). It is noted that liquid manure and sewage sludge promote the development of new shoots. Care must be taken with doses above the leaf carpet. It is recommended instead to work manure into the soil.

In the case of acid soil, the soil should be enhanced with a dose of lime.

Delivery of the Young Plants Grown Out of Root Cuts From a Mother Plant

The new variety 'Igniscum' young plants grown out of root cuts from a mother plant are delivered by plant transport with appropriately equipped transporters. A truck is equipped with a lifting platform. The plants are packed in boxes for shipping on CC roll containers. Before loading is started in the manufacturing enterprise, quality control by an authorized company is to be carried out, so that shipping is carried out with certified documents.

If it is not possible to plant the young plants grown out of root cuts from a mother plant within 24 hours, it must be guaranteed that the plant material receives adequate care.

This includes:

Unloading from the roll containers to a bright site (no storing in dark barns, halls, or cold storage houses).

Avoid draft and direct sunlight.

Supply the plant with water (the plants should be moistened, but not dripping wet, which would result in the standing of the young plants grown out of root cuts from a mother plant in water, thus causing the danger of root rot).

The young plants grown out of root cuts from a mother plant should not be yanked out of their containers by force because that would damage the roots.

Planting of the Young Plants Grown Out of Root Cuts From a Mother Plant

In the year of planting, a culture of young plants grown out of root cuts from a mother plant is not able to assert itself against the accompanying vegetation, which is often abundant in fields and disused areas, due to their fresh and still unlignified shoots. A precondition for optimum cultivation is therefore the preparation of a good nursery bed.

a) Planting time

Planting time always depends on the weather and the climatic conditions of the surface to be planted. In general, with experience, the plant can be cultivated during the entire growing season.

From long-term experience, the planting of perennial plants after May 11-15 is the most favorable point in time.

A further option is to plant already grown young plants grown out of root cuts from a mother plant in the spring or in the autumn. The young plants grown out of root cuts from a mother plant are planted by a vegetable planter into the prepared, slightly moist, pre-manured, crumbly, stone-free and clot-free cropping soil.

The young plants grown out of root cuts from a mother plant must be put into the earth at a depth of at least a root ball, preferably of a root ball plus 2-3 cm.

The space between young plants grown out of root cuts from a mother plant is to be adapted to the mechanical equipment needed for weed control.

After planting, in order to ensure rooting of the young plants grown out of root cuts from a mother plant, it is important to keep the planted area moist; i.e.; in case of draught this area must be irrigated until the young plants grown out of root cuts from a mother plant have rooted.

It is recommended to slightly earth up the plants.

In the year of planting, it is important to provide for sufficient water. Sufficient precipitation is at least 440 mm evenly distributed over the year.

b) Plant spacing 7500 plants are planted per hectare of cropping soil. According to experience, the space between the rim of the field and the plants should be +5 m.

The space between rows is 0.75 m.

The space between plants in a row is 0.80 m.

It is recommended to orientate the rows towards the south in order to benefit from the most effective solar radiation.

In order to avoid a possible touching of the grown plants by a plough or grubber from a neighboring field and a following return to the wild of the plant, it is recommendable to build a root barrier around the planted area.

x . . . 0.80 . . . x . . . 0.80 . . . x . . . 0.80 space between plants, staggered row 0.75 m space between rows .x . . . 0.80 . . . x . . . 180 . . . x space between plants, staggered row 2.50 m, space between lanes x . . .0.80 . . . x . . . 0.80 . . . x . . . 0.80 space between plants 0.75 m space between rows .x . . . 0.80 . . . x . . . 1.80 . . . xspace between plants a) Planters For very small plots, it is recommended to plant manually applying a garden line and a trowel.

In large-scale cultivation, forest planting machines or vegetable planters are applied, which can be adjusted to the required space between plants.

The space between plants and rows is regulated according to the machinery used for care and harvest (track width, trafficability of the field, double row design).

Care of the Young Plants Grown Out of Root Cuts From a Mother Plant

Plant protection

It is decisive for a healthy development of the plants to eliminate and suppress any competing plants in the year of rooting.

Since the new variety 'Igniscum' is regarded a weak competitor in the year of rooting, it is required to avoid and fight weeds in the first year.

It is not recommended to plant directly after ploughing up grassland.

In the year of rooting and, if necessary, in the first year of crop, it is necessary to apply weed control measures in order to guarantee undisturbed development. In doing so it is important to prefer mechanical weed control measures to chemical ones. Precautionary measures include the selection of sites and care of the crop.

a) Preparation (cse soil preparation)
b) Mechanical weed control measures applying a curry-comb, hoe, tined weeder, etc. In the first year, hoe 2-3 times. (When hoeing, be careful that no root parts are displaced by accident).
c) Option of undersown crops (lawn grass or clover)
d) Mulch plants in a bed of straw in the rows (as is done in strawberry cultures); example: 'Amazone' mulcher Since no pests are known to this day, it is not necessary to treat the plantation with pesticides.

However, it is recommended to watch out for infestation by pests in the first years because of the monoculture.

Late Frosts

From experience, a drop in the crop caused by late frosts (May-June) does not influence the crop when harvesting in the autumn. However, it is possible that strong late frosts (May-June) may cause a reduction of the biomass yield (in the case of several harvests per year).

Biomass Harvesting a) According to biomass development, it is possible to harvest several times in the period of growth.
b) In the first year of cultivation (second year after rooting) it is recommended to only hoe the plants, in order to motivate the plant material to produce 'eyes.' The amount of biomass is not significant in the first year. Harvesting can be started with the $2^{nd}$ year ($3^{rd}$ year after planting).

c) Fresh biomass harvesting begins at the end of June/beginning of July in a rhythm of 4-6 weeks, if it is intended not to harvest any dry matter.

d) If it is intended to harvest dry matter, fresh biomass should exclusively be harvested only once. Dry matter should exclusively be harvested in the winter months (January/end of February) with the start of the frost period in order to avoid damaging the young shoots, which under mild weather conditions grow very early below the surface. Harvesting is recommended when the soil is frozen in order to protect the root balls and avoid soil compaction.

Harvesting is carried out as closely as possible above the soil surface (root balls must not be damaged).

Harvesting Machinery

To this date, biomass harvesting has been carried out in experiments using row-independent corn choppers.

It is also possible to use a harvesting machine or a chopper as is used in the forest and lumber industry for harvesting biomass for the production of energy.

The lumber industry already has fully automated wood chip harvesters available.

Ecological Consequences

The cultivation of the new variety 'Igniscum' in fields is characterized by a conservative application of fertilizers and pesticides. This crop cultivation sustainably extends the possibilities of ecological agriculture with a lasting effect.

There is a general observation that the plant is not affected by pests or insects, it is considered self-resistant.

It is claimed:

1. A new and distinct variety of *Fallopia* plant named 'Igniscum,' substantially as shown and described herein.

* * * * *